US011964135B2

United States Patent
Moser et al.

(10) Patent No.: US 11,964,135 B2
(45) Date of Patent: *Apr. 23, 2024

(54) PHARMACEUTICAL PACKAGING RECEPTACLE WITH A LUBRICANT LAYER FOR REMOVAL OF A CHARGE

(71) Applicant: SCHOTT Pharma AG & Co. KGaA, Mainz (DE)

(72) Inventors: Raymond Moser, Engelburg (CH); Stephanie Mangold, Schornsheim (DE)

(73) Assignee: SCHOTT Pharma AG & Co. KGaA, Mainz (DE)

( * ) Notice: Subject to any disclaimer, the term of this patent is extended or adjusted under 35 U.S.C. 154(b) by 545 days.

This patent is subject to a terminal disclaimer.

(21) Appl. No.: 17/193,395

(22) Filed: Mar. 5, 2021

(65) Prior Publication Data

US 2021/0275748 A1 Sep. 9, 2021

(30) Foreign Application Priority Data

Mar. 6, 2020 (EP) .................................. 20161539

(51) Int. Cl.
*A61M 5/31* (2006.01)
*A61M 5/315* (2006.01)

(52) U.S. Cl.
CPC ...... *A61M 5/3129* (2013.01); *A61M 5/31505* (2013.01); *A61M 2005/3103* (2013.01);
(Continued)

(58) Field of Classification Search
CPC ............ A61M 5/3129; A61M 5/31505; A61M 2005/3103; A61M 2205/0222; A61M 2207/00
See application file for complete search history.

(56) References Cited

U.S. PATENT DOCUMENTS

| 4,767,414 A | 8/1988 | Williams et al. |
| 2007/0299402 A1 | 12/2007 | Ishii et al. |

(Continued)

FOREIGN PATENT DOCUMENTS

| EP | 0 920 879 A2 | 6/1999 |
| WO | 2014/190225 A1 | 11/2014 |

OTHER PUBLICATIONS

European Search Report dated Sep. 17, 2020 for European Patent Application No. 20 16 1539 (4 pages).

(Continued)

*Primary Examiner* — Lauren P Farrar
(74) *Attorney, Agent, or Firm* — Taylor IP, P.C.

(57) ABSTRACT

A receptacle includes an elongate barrel section defining a barrel length between an axial position $p_A$ and an axial position $p_B$; side walls each having an inner surface bordering an interior; a layer of a lubricant located on the inner surface; and a charge present in the interior and sealing a cross section of the interior between the inner surfaces of the side walls. An axial position $p_+$ is the axial position closest to $p_B$ at which the charge contacts the layer or the inner surfaces and an axial position $p_-$ is the axial position closest to $p_A$ at which the charge contacts the layer or the inner surfaces. The distance between $p_B$ and $p_+$ divided by the distance between $p_+$ and $p_A$ is in a range from 0 to 2 and a mean thickness of the layer between $p_A$ and p. is at least 10 nm.

20 Claims, 8 Drawing Sheets

(52) U.S. Cl.
CPC ............... *A61M 2005/3131* (2013.01); *A61M 2205/0222* (2013.01); *A61M 2207/00* (2013.01)

(56) References Cited

U.S. PATENT DOCUMENTS

| | | |
|---|---|---|
| 2010/0305513 A1 | 12/2010 | Araki et al. |
| 2017/0182252 A1* | 6/2017 | Hamel ................. B65B 7/2821 |
| 2018/0015225 A1 | 1/2018 | Vogt |

OTHER PUBLICATIONS

European Search Report dated Feb. 13, 2020 for European Patent Application No. 19210764 (5 pages).
Communication pursuant to Article 94(3) EPC for European Patent Application No. 19210764 (4 pages).
European Search Report dated Feb. 7, 2020 for European Patent Application No. 19210762 (4 pages).

\* cited by examiner

US 11,964,135 B2

PHARMACEUTICAL PACKAGING RECEPTACLE WITH A LUBRICANT LAYER FOR REMOVAL OF A CHARGE

CROSS REFERENCE TO RELATED APPLICATIONS

This application claims priority to European Patent Application EP 20161539.0 filed on Mar. 6, 2020, which is incorporated herein by reference.

BACKGROUND OF THE INVENTION

1. Field of the Invention

The present invention generally relates to a receptacle for pharmaceutical packaging containing a charge and having a lubricant layer. In particular, the present invention relates to a receptacle; a process for preparing a disposal product and a use of a lubricant layer in disposal.

2. Description of the Related Art

Pharmaceutical material can be provided in a number of forms and contained in a variety of different containers. In the case of a liquid pharmaceutical material, some common examples are ampules, vials, cartridges and syringes. One widely used format employs a sliding plunger within a container for ejecting a liquid out of an aperture. One approach is to provide a lubricating layer on the inside of the container to facilitate a sliding movement of the plunger.

U.S. Pat. No. 4,767,414 A describes plasma activation of an inner surface prior to application of a layer of silicone lubricant.

European Patent No. EP 0920879 B1 describes a recipe for a silicone-based mixture comprising reactive components and unreactive components.

There persists a need for improved pharmaceutical containers.

SUMMARY OF THE INVENTION

Exemplary embodiments provided according to the present invention at least partially solve one or more of the above-mentioned challenges.

Exemplary embodiments provided according to the present invention provide an improved receptacle for pharmaceutical packaging.

Exemplary embodiments provided according to the present invention provide a receptacle for pharmaceutical packaging which allows an improved fine control for drawing fluid.

Exemplary embodiments provided according to the present invention provide a receptacle for pharmaceutical packaging which exhibits improved transportability with reduced propensity to contaminate.

Exemplary embodiments provided according to the present invention provide a receptacle for pharmaceutical packaging which simultaneously achieves two or more of the following:

Improved fine control for administering fluid or drawing fluid or both;

Improved transportability, with reduced propensity to contaminate;

Improved disposability.

Exemplary embodiments provided according to the present invention provide an improved process for disposing of a receptacle for pharmaceutical packaging.

Exemplary embodiments provided according to the present invention provide a process for disposing of a receptacle for pharmaceutical packaging having less steps, in some embodiments a process which does not require a crushing step.

Exemplary embodiments provided according to the present invention provide a process for disposing of a receptacle for pharmaceutical packaging with reduced risk of contamination, particularly from pharmaceutical liquids and bodily fluids.

Exemplary embodiments provided according to the present invention provide a process for disposing of a receptacle for pharmaceutical packaging with reduced halogen emissions.

In some exemplary embodiments provided according to the present invention, a receptacle for pharmaceutical packaging includes: an elongate barrel section having a direction of elongate extension and an axis in the direction of elongate extension, an axial position p being determined along the axis, the elongate barrel section extending from an axial position $p_A$ to an axial position $p_B$, the elongate barrel section defining a barrel length $L_B$ which is the distance between the axial position $p_A$ and the axial position $p_B$; a first end closer to the axial position $p_A$ than to the axial position $p_B$; a second end closer to the axial position $p_B$ than to the axial position $p_A$; a first aperture at the first end that has a first aperture diameter; a second aperture at the second end that has a second aperture diameter, the first aperture diameter is greater than the second aperture diameter; a plurality of side walls extending over the elongate barrel section, the side walls each having an inner surface bordering an interior, the interior having a diameter; a layer of a lubricant located on at least a part of the inner surface, wherein, at a given axial position p on the axis between the axial position $p_A$ and the axial position $p_B$, a thickness of each side wall, a thickness of the layer, and the diameter of the interior are each determined as an angular mean in a cross-sectional plane perpendicular to the axis at the axial position p; and a charge present in the interior and sealing a cross section of the interior between the inner surfaces of the side walls. An axial position $p_+$ is the axial position closest to the axial position $p_B$ at which the charge contacts the layer or the inner surfaces and an axial position $p_-$ is the axial position closest to the axial position $p_A$ at which the charge contacts the layer or the inner surfaces. A value of the distance between the axial position $p_B$ and the axial position $p_+$ divided by the distance between the axial position $p_+$ and the axial position $p_A$ is in a range from 0 to 2. A mean thickness of the layer determined between the axial position $p_A$ and the axial position $p_-$ is at least 10 nm. At least one criteria is satisfied, the at least one criteria being selected from the group consisting of: the length $L_B$ is in a range from 3 cm to 20 cm; a mean value of the diameter of the interior determined over a range from the axial position $p_A$ to the axial position $p_B$ is in a range from 0.4 cm to 4 cm; a mean thickness of one of the sidewalls determined over a range from the axial position $p_A$ to the axial position $p_B$ is in a range from 0.3 mm to 4.5 mm; and the volume of the interior is in a range from 0.1 to 150 ml.

In some exemplary embodiments provided according to the present invention, a process for preparing a disposal product is provided. The process includes providing a receptacle and converting the receptacle into the disposal product. The receptacle includes: an elongate barrel section having a direction of elongate extension and an axis in the direction of elongate extension, an axial position p being determined along the axis, the elongate barrel section extending from an axial position $p_A$ to an axial position $p_B$, the elongate barrel section defining a barrel length $L_B$ which is the distance between the axial position $p_A$ and the axial position $p_B$; a first end closer to the axial position $p_A$ than to the axial position $p_B$; a second end closer to the axial position $p_B$ than to the axial position $p_A$; a first aperture at the first end that has a first aperture diameter; a second aperture at the second end that has a second aperture diameter, the first aperture diameter is greater than the second aperture diameter; a plurality of side walls extending over the elongate barrel section, the side walls each having an inner surface bordering an interior, the interior having a diameter; a layer of a lubricant located on at least a part of the inner surface, wherein, at a given axial position p on the axis between the axial position $p_A$ and the axial position $p_B$, a thickness of each side wall, a thickness of the layer, and the diameter of the interior are each determined as an angular mean in a cross-sectional plane perpendicular to the axis at the axial position p; and a charge present in the interior and sealing a cross section of the interior between the inner surfaces of the side walls. An axial position $p_+$ is the axial position closest to the axial position $p_B$ at which the charge contacts the layer or the inner surfaces and an axial position $p_-$ is the axial position closest to the axial position $p_A$ at which the charge contacts the layer or the inner surfaces. A value of the distance between the axial position $p_B$ and the axial position $p_+$ divided by the distance between the axial position $p_+$ and the axial position $p_A$ is in a range from 0 to 2. A mean thickness of the layer determined between the axial position $p_A$ and the axial position p. is at least 10 nm. At least one criteria is satisfied, the at least one criteria being selected from the group consisting of: the length $L_B$ is in a range from 3 cm to 20 cm; a mean value of the diameter of the interior determined over a range from the axial position $p_A$ to the axial position $p_B$ is in a range from 0.4 cm to 4 cm; a mean thickness of one of the sidewalls determined over a range from the axial position $p_A$ to the axial position $p_B$ is in a range from 0.3 mm to 4.5 mm; and the volume of the interior is in a range from 0.1 to 150 ml.

In some exemplary embodiments provided according to the present invention, a receptacle for pharmaceutical packaging includes: an elongate barrel section having a direction of elongate extension and an axis in the direction of elongate extension, an axial position p being determined along the axis, the elongate barrel section extending from an axial position pA to an axial position pB; a first end closer to the axial position pA than to the axial position pB; a second end closer to the axial position pB than to the axial position pA; a first aperture at the first end that has a first aperture diameter; a second aperture at the second end that has a second aperture diameter, the first aperture diameter is greater than the second aperture diameter; a plurality of side walls extending over the elongate barrel section, the side walls each having an inner surface bordering an interior that defines a volume; a layer of lubricant placed on at least a part of the inner surface; and a charge present in the interior and sealing a cross section of the interior between the inner surfaces of the side walls, the charge being displaceable within the interior between the axial position pB and the axial position pA and removeable from the interior by pulling the charge out of the interior through the first aperture. A variable dynamic friction is defined between the charge and the side walls as the charge is displaced between the axial position pB and the axial position pA, the dynamic friction increasing as the charge is displaced in a first region of the interior in a direction from the axial position pB toward the axial position pA and decreasing as the charge is displaced in a second region of the interior in the direction from the axial position pB toward the axial position pA.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
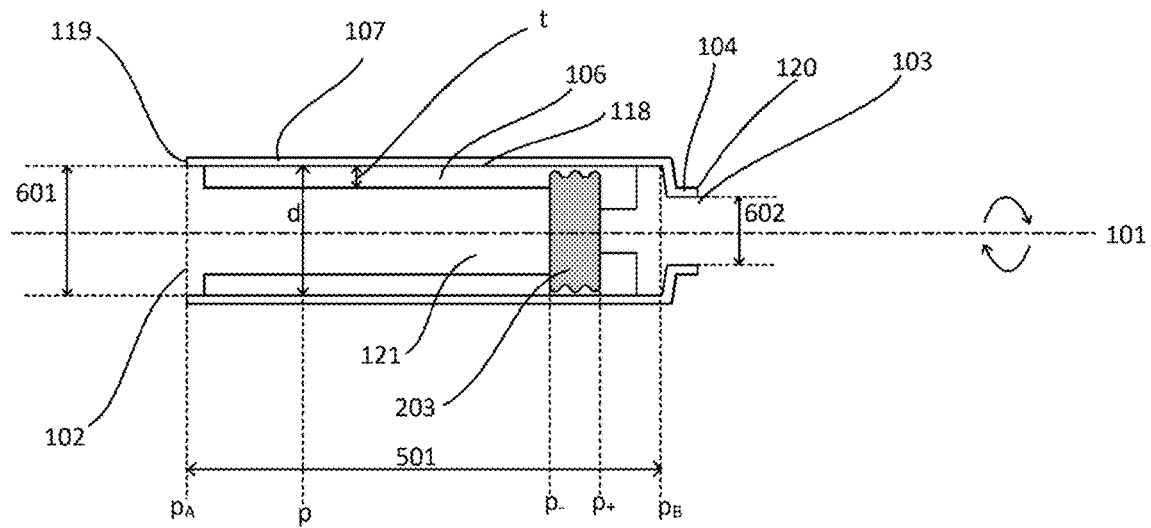
FIG. 1 illustrates a cross-sectional view of an exemplary embodiment of a receptacle in the form of a cartridge, provided according to the present invention.

The following exemplary embodiments represent some of the arrangements provided according to the present invention.

A receptacle for pharmaceutical packaging, the receptacle having an elongate barrel section, wherein:
 a. the receptacle has a first end and a second end;
 b. the elongate barrel section has a direction of elongate extension and an axis in the direction of elongate extension;
 c. an axial position p is determined along the axis;
 d. the elongate barrel section extends from an axial position $p_A$ to an axial position $p_B$;
 e. the barrel length $L_B$ is the distance between $p_A$ and $p_B$;
 f. the first end is closer to $p_A$ than to $p_B$;
 g. the second end is closer to $p_B$ than to $p_A$;
 h. the receptacle has a first aperture at the first end and a second aperture at the second end;
 i. the first aperture has a first aperture diameter, the second aperture has a second aperture diameter and the first aperture diameter is greater than the second aperture diameter, such as at least 10% greater, at least 50% greater, at least 100% greater, or at least 500% greater;
 j. the receptacle has a side wall extending over the elongate barrel section, the side wall having an inner surface bordering an interior, the interior having a diameter;

k. a layer of a lubricant is located on at least a part of the inner surface;
l. at a given axial position p on the axis between $p_A$ and $p_B$, the following:
   i. the thickness of the side wall,
   ii. the thickness of the layer, and
   iii. the diameter of the interior,
   are each determined as an angular mean in a cross-sectional plane perpendicular to the axis at the axial position p;
m. a charge is present in the interior sealing a cross section of the interior between the inner surfaces of the side walls;
n. an axial position $p_+$ is the axial position closest to $p_B$ at which the charge contacts the layer or the inner surface;
o. an axial position $p_-$ is the axial position closest to $p_A$ at which the charge contacts the layer or the inner surface;
p. the value of the distance between $p_B$ and $p_+$ divided by the distance between $p_+$ and $p_A$ is in the range from 0 to 2, such as from 0.001 to 1, from 0.01 to 0.7, from 0.05 to 0.5, from 0.1 to 0.4, or from 0.2 to 0.3;
q. the mean thickness of the layer determined between $p_A$ and $p_-$ is at least 10 nm, such as at least 20 nm, at least 30 nm, at least 40 nm, or at least 50 nm; and
r. one or more criteria are satisfied, the criteria being selected from the group consisting of:
   i. The length $L_B$ is in the range from 3 to 20 cm;
   ii. The mean value of the diameter of the interior determined over the range $p_A$ to $p_B$ is in the range from 0.4 to 4 cm;
   iii. The mean thickness of the sidewall determined over the range $p_A$ to $p_B$ is in the range from 0.3 to 4.5 mm;
   iv. The volume of the interior is in the range from 0.1 to 150 ml.

In some embodiments, the mean thickness of the layer determined between $p_A$ and $p_-$ is at most 300 nm, such as at most 250 nm, at most 200 nm, at most 150 nm, or at most 100 nm.

In some embodiments, the maximum thickness of the layer determined between $p_A$ and $p_-$ is at least 20 nm, such as at least 30 nm, at least 40 nm, or at least 60 nm.

In some embodiments, the maximum thickness of the layer determined between $p_A$ and $p_-$ is at most 400 nm, such as at most 350 nm, at most 300 nm, or at most 250 nm.

In some embodiments, a continuous portion X between $p_A$ and $p_-$ having a length of at least 50%, such as at least 60%, or at least 70%, of the length from $p_A$ and $p_-$ has a minimum thickness of at least 5 nm, such as at least 10 nm, at least 20 nm, or at least 40 nm In some embodiments, a continuous portion X between $p_A$ and $p_-$ having a length of at least 50%, such as at least 60%, or at least 70%, of the length from $p_A$ and $p_-$ has a minimum thickness of at most 300 nm, such as at most 250 nm, at most 200 nm, or at most 150 nm.

In some embodiments, a continuous portion X between $p_A$ and $p_-$ having a length of at least 50%, such as at least 60%, or at least 70%, of the length from $p_A$ and $p_-$ has a minimum thickness and a maximum thickness and the difference between the minimum thickness and the maximum thickness is at least 5 nm, such as at least 10 nm, at least 20 nm, or at least 30 nm.

In some embodiments, a continuous portion X between $p_A$ and $p_-$ having a length of at least 50%, such as at least 60%, or at least 70%, of the length from $p_A$ and $p_-$ has a minimum thickness and a maximum thickness and the difference between the minimum thickness and the maximum thickness is at most 300 nm, such as at most 250 nm, at most 200 nm, or at most 150 nm.

In some embodiments, the maximum thickness of the layer determined between $p_A$ and $p_-$ is at an axial position closer to $p_-$ than to $p_A$.

In some embodiments, the mean thickness of the layer determined between $p_B$ and $p_+$ is at least 1.5 times the mean thickness of the layer determined between $p_A$ and $p_-$, such as at least 2 times, or at least 3 times.

In some embodiments, the maximum thickness of the layer determined between $p_B$ and $p_+$ is at least 1.5 times the maximum thickness of the layer determined between $p_A$ and $p_-$, such as at least 2 times, or at least 3 times.

In some embodiments, the first aperture diameter is at least 80% of the average diameter of the interior, such as at least 90%, at least 95%, or at least 99%.

In some embodiments, the second aperture diameter is at most 70% of the average diameter of the interior, such as at most 50%, at most 40%, or at most 30%.

In some embodiments, the charge comprises a halogen, such as F, Cl, Br and/or I.

In some embodiments, the halogen is present in a polymer.

In some embodiments, the halogen is present in a coating of the charge.

In some embodiments, the maximum force required to remove the charge from the receptacle through the first aperture is not more than 10 N, such as not more than 8 N, or not more than 7 N. The maximum force may be determined according to the removal process presented in the drawings.

In some embodiments, the maximum force required to remove the charge from the receptacle through the first aperture is at least 4 N, such as at least 5 N, or at least 6 N. The maximum force may be determined according to the removal process presented in the drawings.

In some embodiments, the maximum force required to remove the charge from the receptacle through the first aperture occurs when the front of the charge is closer to $p_A$ than to $p_B$. The maximum force may be determined according to the removal process presented in the drawings.

In some embodiments:
s. movement of the charge along the axis in the direction from $p_B$ to $p_A$ is resisted by a dynamic friction g, g being a function of the axial position of the front of the charge;
t. g has a maximum value $g_{MAX}$ at an axial position $p_{MAX}$;
u. the minimum value of g between $p_+$ and $p_{MAX}$ is $g_{MIN}$ and is at an axial position $p_{MIN}$; and
v. one or more of the following criteria are satisfied:
   i. $F_{MAX}$ is in the range from 2 to 10 N, such as from 3 to 8 N, or from 3.5 to 7 N;
   ii. $F_{MIN}$ is in the range from 0.5 to 5 N, such as in the range from 1 to 4 N, or in the range from 2 to 3 N;
   iii. $p_{MAX}$ is closer to $p_A$ than to $p_B$;
   iv. $p_{MIN}$ is closer to $p_B$ than to $p_A$;
   v. $g_{MAX}/g_{MIN}$ is in the range from 1.1 to 4, such as from 1.2 to 3.5, or from 1.5 to 3.

Dynamic friction may be determined according to the removal process presented in the drawings.

In some embodiments, the following combinations of previously described features are satisfied: i., ii., i.+ii., iii., i.+iii., ii.+iii., i.+ii.+iii., iv., i.+iv., ii.+iv., i.+ii.+iv., iii.+iv., i.+iii.+iv., ii.+iii.+iv., i.+ii.+iii.+iv., v., i.+v., ii.+v., i.+ii.+v., iii.+v., i.+iii.+v., ii.+iii.+v., i.+ii.+iii.+v., iv.+v., i.+iv.+v., ii.+iv.+v., i.+ii.+iv.+v., iii.+iv.+v., i.+iii.+iv.+v., ii.+iii.+iv.+v., i.+ii.+iii.+iv.+v.

In some embodiments, the side wall comprises a plastic or a glass or both.

In some embodiments, the lubricant comprises one or more silicone oils. In some embodiments, the lubricant comprises in total at least 5 wt. %, such as at least 15 wt. %, or at least 25 wt. % of one or more silicone oils, based on the total weight of the lubricant of the layer.

In some embodiments, the one or more silicone oils are at least partially contained in a matrix, wherein the matrix is bound to the inner surface.

In some embodiments, the matrix is a polymer, such as a crosslinked polymer.

In some embodiments, the polymer comprises SiO-containing repeating units. An exemplary polymer is a polysiloxane, such as a crosslinked polysiloxane.

In some embodiments, the interior is cylindrical or truncated conical over the elongate barrel section. An exemplary truncated cone has a cone aperture in the range from 0.040 to 0.4°, such as in the range from 0.08° to 0.25°, or in the range from 0.10 to 0.2°.

In some embodiments, an attachment element is provided at an aperture. The attachment element may be at an end, such as at the second end. An exemplary attachment element is adapted and arranged for attaching one or both selected from the group consisting of a needle and a tube. Some exemplary attachment elements are a screw thread, a latch, a Luer fitting and a bayonet-style fitting.

In some embodiments, the receptacle contains a liquid pharmaceutical composition present in a section of the interior between $p_+$ and $p_B$.

In some exemplary embodiments, a process for preparing a disposal product includes:
w. Providing a receptacle according to any of the previously described embodiments; and
x. Converting the receptacle into a disposal product.

In some embodiments, the process includes:
Removing the charge from the receptacle through the first aperture.

In some embodiments, the process includes a heating step.

In some embodiments, the process includes an oxidation step.

In some embodiments, the disposal product comprises less than 50 ppm of halogen by mass, such as less than 40 ppm, less than 30 ppm, less than 10 ppm, or less than 5 ppm.

In some exemplary embodiments provided according to the present invention, a use of a lubricant layer having a mean thickness of at least 10 nm for improving the disposal of a used pharmaceutical receptacle is provided.

In some embodiments, a disposal product having a reduced halogen content is obtainable from the disposal.

Diameters, Layer Thicknesses and Roughness

The axis of the receptacle is used to determine the axial position. At a given axial position, the side wall is a perimeter having a thickness lying in a cross-sectional plane perpendicular to the axis, likewise for the lubricant layer. Internal diameter, thickness of the lubricant layer, thickness of the side wall and surface roughness at a given point along the axis may be mean values determined around a perimeter. A mean around a perimeter is an angular mean. An angular mean may be determined by measuring at 8 points around the perimeter, the 8 points being separated by equal angles.

Receptacle

An exemplary receptacle is adapted and arranged to contain a liquid pharmaceutical composition. Some exemplary receptacles are syringes, syringe barrels, cartridges and vials.

In some embodiments, the receptacle may be provided by:
a. Providing a receptacle having a first end and a second end, the receptacle containing a liquid pharmaceutical composition and a charge located closer to the first end than to the second end;
b. Moving the charge to a position closer to the second end than to the first end, thereby ejecting the liquid pharmaceutical composition from the second end.

The receptacle may be a used pharmaceutical receptacle.

An exemplary receptacle has an attachment element, which may be at an end, such as at the second end. An exemplary attachment element is adapted and arranged for attaching a needle or tube. A needle or tube may be attached to the receptacle in the assembly.

Elongate Barrel Section

The receptacle has an elongate barrel section. The elongate barrel section denominates a section of the receptacle. The receptacle may have further sections outside of the elongate barrel section. Another term for an elongate barrel section is a tube section. An exemplary elongate barrel section is tubular.

Exemplary embodiments of the elongate barrel section and the axis are described herein in mathematical terms, for example as axes of symmetry, rotation or revolution, surfaces and solids of revolution and shapes such as cylinders and truncated cones. These embodiments are to be understood as allowing some variation from these precise mathematical concepts. Suitable variations from the mathematic concepts are those which do not inhibit the elongate barrel section from functioning as a plunger system in cooperation with a charge.

The elongate barrel section has an axis. The axis may be an axis of rotation for the elongate barrel section. The axis may be an axis of revolution for the elongate barrel section. The side wall may be a solid of revolution about the axis. The inner surface may be a surface of revolution about the axis. The layer may be a solid of revolution about the axis.

The axis defines an axial position p. The axial position p is an axial position along the axis. As used herein, the symbol p denotes an axial position in general terms and specific axial positions are denoted by the letter p with a subscript.

An axial position p along the axis is used as a parameter to describe the locations of points or cross-sections along the elongate barrel section, for example on the side wall. The axial position of a point not on the axis is found by projecting the point onto the axis by a displacement vector perpendicular to the axis. A cross section is a plane perpendicular to the axis. The axial position of a cross section is found at the point where the cross section meets the axis.

The elongate barrel section extends from an axial position $p_A$ to an axial position $p_B$. The elongate barrel section is bordered by a cross section at $p_A$ and a cross section at $p_B$.

The receptacle has a side wall extending over the elongate barrel section. The side wall has an inner surface. The inner surface borders an interior. Exemplary shapes for the side wall are a hollow cylinder, a hollow prism and a hollow truncated cone. An exemplary hollow truncated cone has a diameter which decreases from $p_A$ to $p_B$. Exemplary shapes for the interior are a cylinder, a prism and a truncated cone. An exemplary truncated cone has a diameter which decreases from $p_A$ to $p_B$.

The inner surface may be smooth, but may have some roughness.

The thickness of the side wall may be measured as a difference in radial distance from the axis of the inner surface and an outer surface of the side wall.

Exemplary materials for the side wall are polymers and glasses.

In some embodiments, the side wall comprises a polymer, and may be made out of a polymer. The polymer may be one or both selected from the group consisting of: one or more cyclic olefin copolymers and one or more cyclic olefin polymers. In some embodiments, the polymer is at least 30 wt. % of the side wall, such as at least 50 wt. %, at least 80 wt. %, or about 100 wt. %.

In some embodiments, the side wall comprises a glass, and may be made of a glass. An exemplary glass comprises one or more selected from the group consisting of: silicon, boron and aluminium. One exemplary glass comprises boron and silicon. One exemplary glass is a borosilicate glass. One exemplary glass comprises aluminium and silicon. One exemplary glass is an aluminosilicate glass. In some embodiments, the glass is at least 30 wt. % of the side wall, such as at least 50 wt. %, at least 80 wt. %, or about 100 wt. %.

Lubricant Layer

The layer of lubricant is located on the inner surface of the side wall. The lubricant layer may extend over the entire elongate barrel section or just a part of it.

An exemplary lubricant is a silicone-based lubricant.

An exemplary lubricant comprises one or more polysiloxanes.

An exemplary lubricant comprises one or more silicone oils, such as a total content of silicone oils in the range from 10 to 50 wt. %, in the range from 20 to 40 wt. %, or in the range from 25 to 35 wt. %, based on the total weight of the lubricant. An exemplary silicone oil is a poly dimethyl silicone.

An exemplary lubricant comprises a crosslinked poly siloxane matrix, such as a total content of crosslinked poly siloxane matrix in the range from 50 to 90 wt. %, in the range from 60 to 80 wt. %, or in the range from 65 to 75 wt. %, based on the total weight of the lubricant.

An exemplary lubricant may be prepared from a mixture comprising one or more, such as all, of the following:

a reactive polysiloxane
an unreactive polysiloxane
a catalyst
a diluent.

An exemplary reactive polysiloxane is adapted and arranged to undergo a cross-linking reaction to obtain a cross-linked network. The cross-linking may be catalyzed by the catalyst.

An exemplary unreactive polysiloxane does not undergo a cross-linking reaction. An exemplary unreactive polysiloxane comprises one or more alkyl groups. A further exemplary unreactive polysiloxane is fully substituted with alkyl groups.

An exemplary catalyst catalyzes a reaction to cross-link polysiloxanes.

An exemplary diluent solves one or more of the other constituents of the mixture. An exemplary diluent is silicon based. An exemplary diluent is a short chain polysiloxane, which may have 6 repeat units or less. An exemplary diluent is hexamethyl disiloxane.

An exemplary lubricant contains not more than 10 wt. % water, based on the total weight of the lubricant, such as not more than 5 wt. %, or not more than 1 wt. %.

In some embodiments, the layer extends over at least 70%, such as at least 80%, at least 90%, or about 100% of the length of the elongate barrel section. In some embodiments, the lubricant extends over 20 to 60% of the length $L_B$ of the elongate barrel section.

Exemplary methods for applying the layer are spreading and wiping with a suitable tool.

The thickness of the layer may be measured as a difference in radial distance from the axis of an inner surface of the layer and the inner surface of the side wall.

The layer of lubricant can be cured after application. Exemplary curing can be thermal or radiation induced or a combination of both. Some exemplary ways of curing are application of UV radiation and application of IR radiation.

Liquid Pharmaceutical Composition

The receptacle is for pharmaceutical packaging. An exemplary receptacle is adapted and arranged to contain a liquid.

A liquid pharmaceutical composition may comprise an active compound.

A liquid pharmaceutical composition is a fluid.

An exemplary amount of liquid pharmaceutical composition is in the range from 0.001 to 10 ml, such as in the range from 0.01 to 5 ml, in the range from 0.05 to 1 ml, in the range from 0.1 to 0.8 ml, or in the range from 0.2 to 0.5 ml.

Charge

The elongate barrel section is adapted and arranged to accommodate a charge. An exemplary charge is adapted and arranged to be accommodated in the elongate barrel section. The elongate barrel section and the charge may be complementary such that the charge can move within the interior in a direction parallel to the axis.

An exemplary charge is made of an elastic material or comprises a part made of an elastic material. The charge may be adapted and arranged to seal a cross-section of the interior. The charge may be adapted and arranged to move inside the receptacle, such as along the axis defined by the elongate extension of the receptacle. When inside the receptacle, movement of the charge may be resisted by a frictional force between the charge and an inside surface of the receptacle.

The charge may be attached to an elongate rod adapted and arranged to push or pull the charge in a direction parallel to the axis.

An exemplary charge is a plunger.

An exemplary charge comprises a halogen, such as F, Cl, Br or I. An exemplary charge may comprise two or more of the aforementioned halogens. The halogen may be present in a polymer compound, for example in a brominated or chlorinated polymer. Exemplary polymers may comprise one or more isobutylene structural units, the isobutylene structural unit being halogenated or non-halogenated. Exemplary polymers may comprise one or more isoprene structural units, the isoprene structural unit being halogenated or non-halogenated. An exemplary polymer is a chlorinated or brominated isobutylene isoprene copolymer. Isobutylene isoprene copolymers may comprise from 95% to 99.5 wt. % isobutylene structural units, such as 96 to 99 wt. %, or 97.5 to 98.5 wt. %; and from 0.5 to 5 wt. % isoprene structural units, such as 1 to 4 wt. %, or 1.5 to 2.5 wt. %.

In some embodiments, the halogen content may be present in a coating of the charge, such as a coating adapted and arranged to contact with the inner surface of the side wall.

Charge Axial Position

When in position in the receptacle, the charge makes contact with the layer or the inner surface or both. The front end of the charge is the point of forwardmost contact of the charge with the layer or the inner surface. The back end of the charge is the point of backmost contact of the charge with the layer or the inner surface. The front end is closer to $p_B$ than is the back end. The front end is further from $p_A$ than is the back end. The charge axial position is the axial position of the front end.

The distance between the front end and the back end of the charge is the charge length $L_C$.

Frictional Forces

The movement of the charge within the receptacle is accompanied by a frictional force between the charge and the inner surface of the side wall and or the layer. The frictional force comprises both a stiction, which resists the setting in motion of the charge relative to the receptacle, and a dynamic friction, which acts whilst the charge is in movement.

The dynamic friction is dependent on the charge axial position. The dynamic friction at a given charge axial position p may be determined by starting the charge at charge axial position $p_+$ and moving the charge from $p_+$ towards $p_A$ at a constant speed of 100 mm/minute. The value of dynamic friction at charge axial position p is the force required to maintain the speed of the charge at 100 mm/minute when the charge is at charge axial position p. A method for determining the dynamic friction is presented in the drawings.

Luer Fitting

Exemplary receptacles have a Luer fitting, such as at the second end. An exemplary Luer fitting is compatible with ISO 80369. Exemplary Luer fittings are Luer lock fittings and slip tip fittings. In some embodiments, the receptacle has a Luer lock fitting. In some embodiments, the receptacle has a slip tip fitting. An exemplary Luer fitting is a male Luer fitting. Exemplary Luer lock fittings are one-piece Luer lock fittings and two-piece Luer lock fittings. In some embodiments, the receptacle has a one-piece Luer lock fitting. In some embodiments, the receptacle has a two-piece Luer lock fitting.

Disposal

Exemplary embodiments provided according to the present invention provide a process for preparing a disposal product comprising the following steps:
 a. providing a receptacle;
 b. converting the receptacle into a disposal product.

In some embodiments, the charge is removed from the receptacle, such as through the first aperture.

In some embodiments, the process comprises one or more selected from the following: an oxidation, a heating, a combustion, an incineration. At least one of those elements may be performed on the receptacle once the charge has been removed from the receptacle.

An exemplary disposal product is a combustion product. An exemplary product is a gas, such as with suspended solid particles. An exemplary disposal product contains less than 5 ppm of halogen by mass, such as less than 4 ppm or less than 3 ppm.

In some embodiments, the conversion of the receptacle into a disposal product comprises the following steps:
 c. removing the charge from the receptacle;
 d. combusting the receptacle without the charge.

Exemplary embodiments provided according to the present invention are now further elucidated by way of drawings. The drawings are exemplary and do not limit the scope of the present invention. Some features of the figures are shown FIG. 1 shows a cross-sectional view of a cartridge embodiment of the receptacle 100 provided according to the present invention. The receptacle 100 has a first end 119 and a second end 120. At the first end 119 is a first aperture 102. At the second end 120 is a second aperture 103. There may be present at the second end 120 an attachment element 104, which may be of the Luer Lock type for attaching a needle fitting. The receptacle 100 has an elongate barrel section 501 extending from an axial position $p_A$ to an axial position $p_B$. The distance between $p_A$ and $p_B$ is the length $L_B$ of the elongate barrel section 501. For simplicity, the elongate barrel section 501 is shown as a hollow cylinder. As an exemplary alternative, it may also have a hollow truncated conical shape with a greater diameter at $p_A$ than at $p_B$. The axis 101 is in the direction of elongate extension of the receptacle 100 and is the axis of rotation of the elongate barrel section 501. The side wall 107 has an inner surface 118, on which is present a layer 106 of lubricant. The side wall 107 borders the interior 121. The layer 106 extends over some, but not all of the side wall 107, not reaching the ends $p_A$ and $p_B$. Axial positions along the receptacle 100 are measured along the axis 101. Axial positions may be given with reference to $p_+$ as a fiduciary zero point. Shown is a general axial position p as well as the internal diameter d between of the inner surfaces 118 of the side walls 107 at that axial position. The thicknesses t is shown for a general position. The charge 203, in this case a bromo-butyl rubber stopper, is present in the interior 121 with its front end at an axial position $p_+$ and its back end at an axial position p. The layer 106 present in the section of the interior between $p_+$ and $p_B$ is thicker than the layer 106 present in the section of the interior between $p_-$ and $p_A$. The thickness of the layer 106 in the section between $p_-$ and $p_A$ satisfies the previously described requirements. Some liquid pharmaceutical composition (not shown) may be present in the section between $p_+$ and $p_B$.

Figure 2:
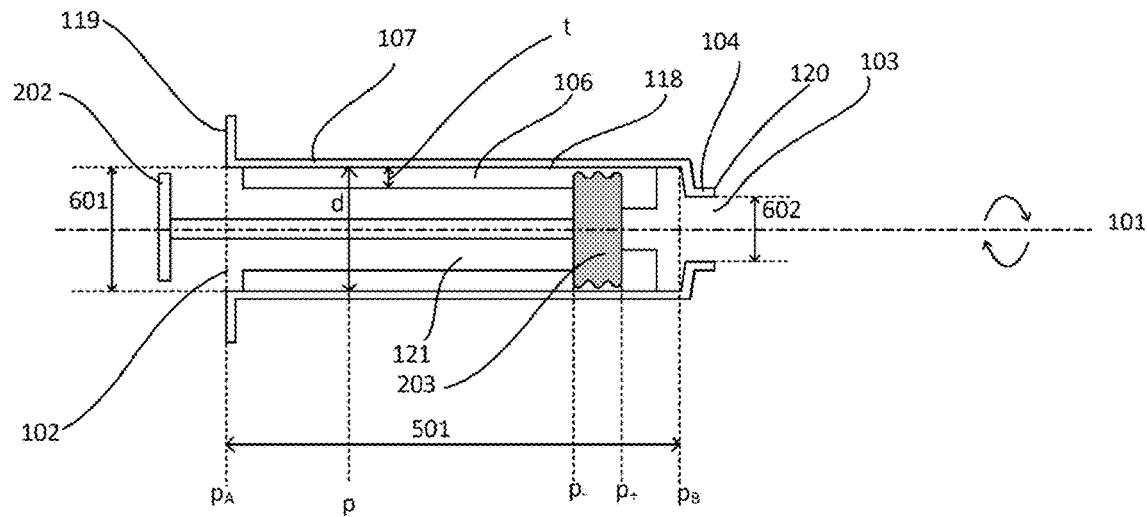
FIG. 2 illustrates a cross-sectional view of an exemplary embodiment of a receptacle in the form of a syringe, provided according to the present invention.

FIG. 2 shows a cross-sectional view of a syringe embodiment of the receptacle 100 provided according to the present invention. The receptacle 100 has a first end 119 and a second end 120. At the first end 119 is a first aperture 102 and an outwardly protruding flange 105. At the second end 120 is a second aperture 103. There may be present at the second end 120 an attachment element 104, such as of the Luer Lock type for attaching a needle fitting. The receptacle 100 has an elongate barrel section 501 extending from an axial position $p_A$ to an axial position $p_B$. The distance between $p_A$ and $p_B$ is the length $L_B$ of the elongate barrel section 501. For simplicity, the elongate barrel section 501 is shown as a hollow cylinder. As an exemplary alternative, it may also have a hollow truncated conical shape with a greater diameter at $p_A$ than at $p_B$. The axis 101 is in the direction of elongate extension of the receptacle 100 and is the axis of rotation of the elongate barrel section 501. The side wall 107 has an inner surface 118, on which is present a layer 106 of lubricant. The side wall 107 borders the interior 121. The layer 106 extends over some, but not all of the side wall 107, not reaching the ends $p_A$ and $p_B$. Axial positions along the receptacle 100 are measured along the axis 101. Axial positions may be given with reference to $p_+$ as a fiduciary zero point. Shown is a general axial position p as well as the internal diameter d between of the inner surfaces 118 of the side walls 107 at that axial position. The thicknesses t is shown for a general position. The charge 203, in this case a bromo-butyl rubber stopper, is present in the interior 121 with its front end at an axial position $p_+$ and its back end at an axial position $p_-$. The charge 203 has an attached elongate rod 202 for pushing or pulling the charge 203 along the axis 101. The layer 106 present in the section of the interior between $p_+$ and $p_B$ is thicker than the layer 106 present in the section of the interior between $p_-$ and $p_A$. The thickness of the layer 106 in the section between $p_-$ and $p_A$ satisfies the previously described requirements. Some liquid pharmaceutical composition may be present in the section between $p_+$ and $p_B$.

Figure 3:
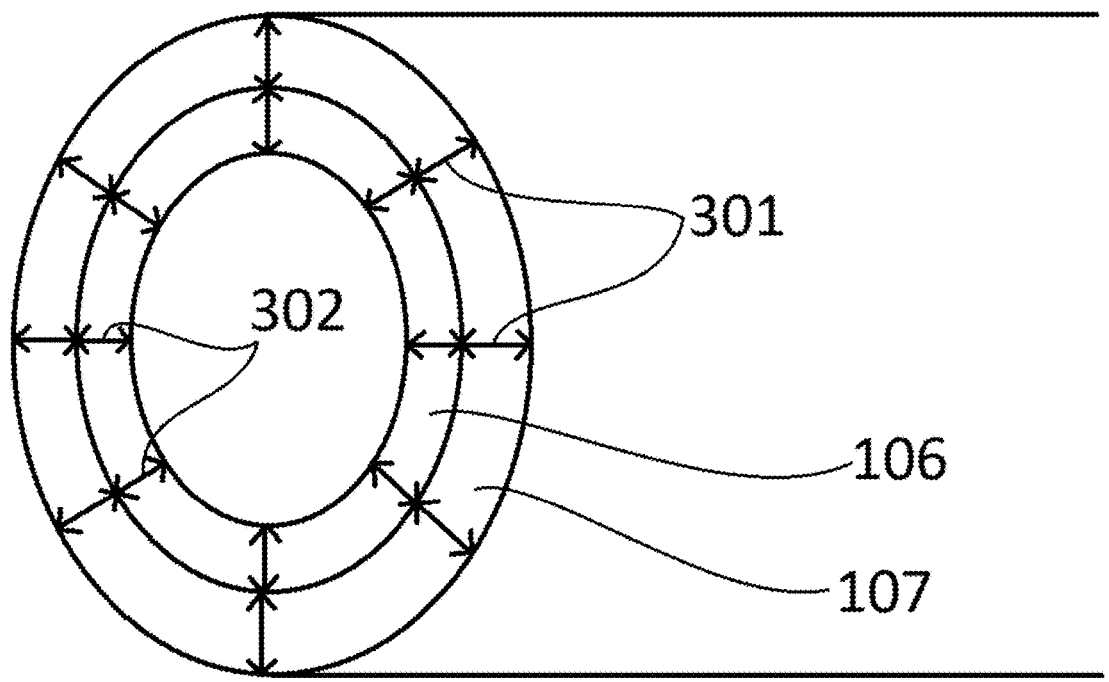
FIG. 3 illustrates a cross-sectional view through the receptacle at an axial position p along an axis.

FIG. 3 shows a cross-sectional view through the receptacle 100 at an axial position p along the axis 101. The side wall 107 and the lubricant layer 106 are shown as concentric circular bands. The thickness 301 of the side wall 107 and the thickness 302 of the lubricant layer 106 are each shown at 8 equidistant points around the circle. A thickness of a side wall 107 or a layer 106 of lubricant at an axial position p is a mean of the thickness around the circle. This is measured as the mean of a number of equally spaced sample points around the circle, in this case 8.

FIGS. 4A to 4F show the process of removing the charge 203 from the receptacle 100. The series of figures demonstrates how the charge 203 may be pulled in a single motion along the axis 101 of the receptacle 100 at a constant speed of 100 mm/min. The process presented can also be used to construct a profile of the dynamic friction between the charge 203 and the side wall 107/lubricant layer 106 as a function of axial position along the axis 101. Because the movement is performed in a single push, a stiction force is only relevant for the start point. Throughout the series, the axial position of the charge is that of its front end.

Figure 4A:
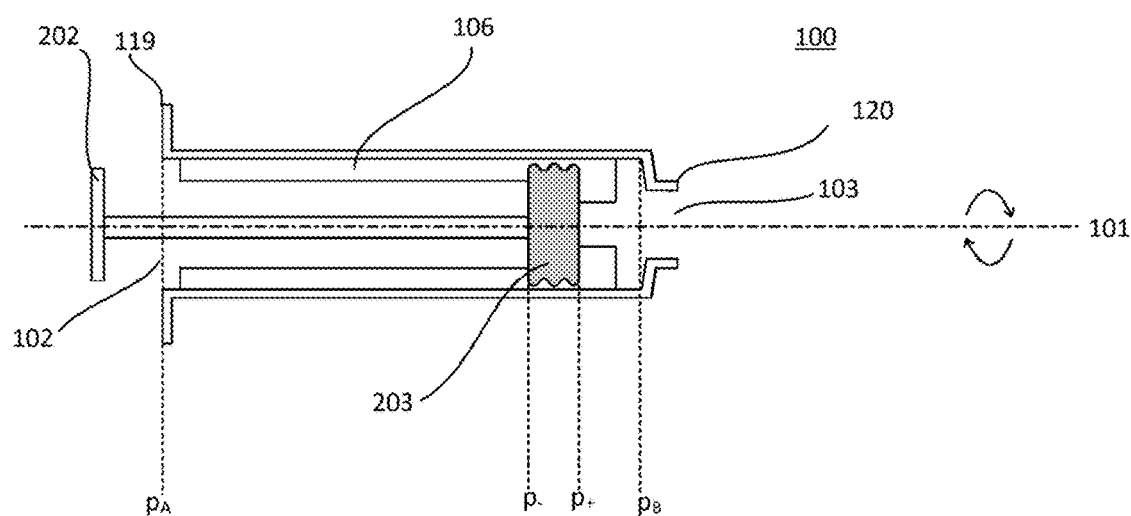
FIGS. 4A to 4F illustrate a process of removing a charge from the receptacle.

FIG. 4A shows a receptacle 100 provided according to the present invention ready for the charge 203 to be removed. The receptacle 100 is as described in FIG. 2. The charge 203 is in axial position $p_+$, towards the second end 120 of the receptacle.

Figure 4B:
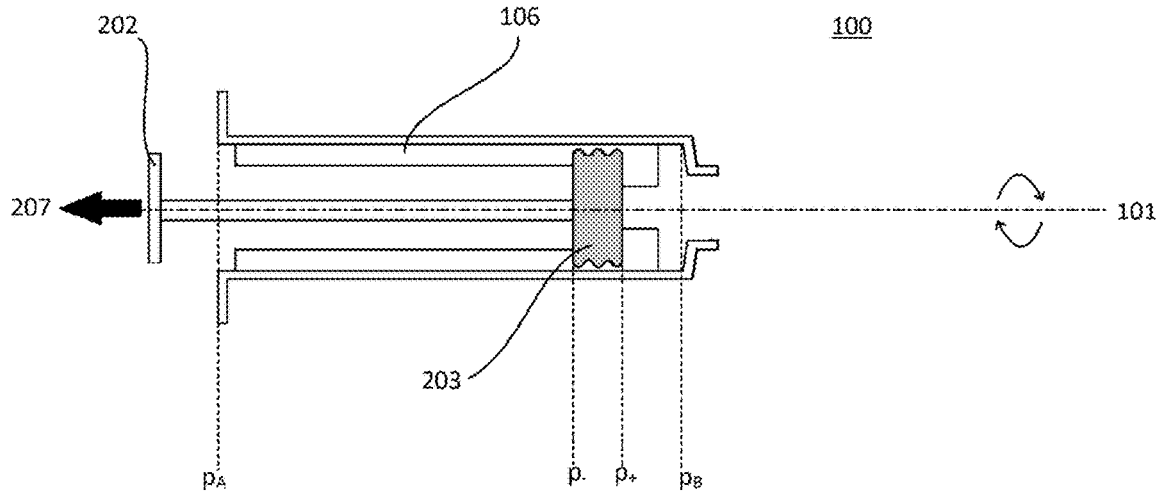

FIG. 4B shows the receptacle 100 of FIG. 2A, in which a pulling force 207 is applied to the elongate rod 202 in a direction along the axis 101 towards the first end 119. The force 207 is transferred to the charge 203. In the figure, the force 207 is inferior to the stiction force at the initial axial position $p_+$ and the charge 203 is at rest, with the pushing force 207 cancelled out by the static frictional force between the charge 203 and the side walls 207/lubricant layer 106. The stiction force at the axial position 201 is determined as the force 207 at which the charge 203 starts to move along the axis 101.

Figure 4C:
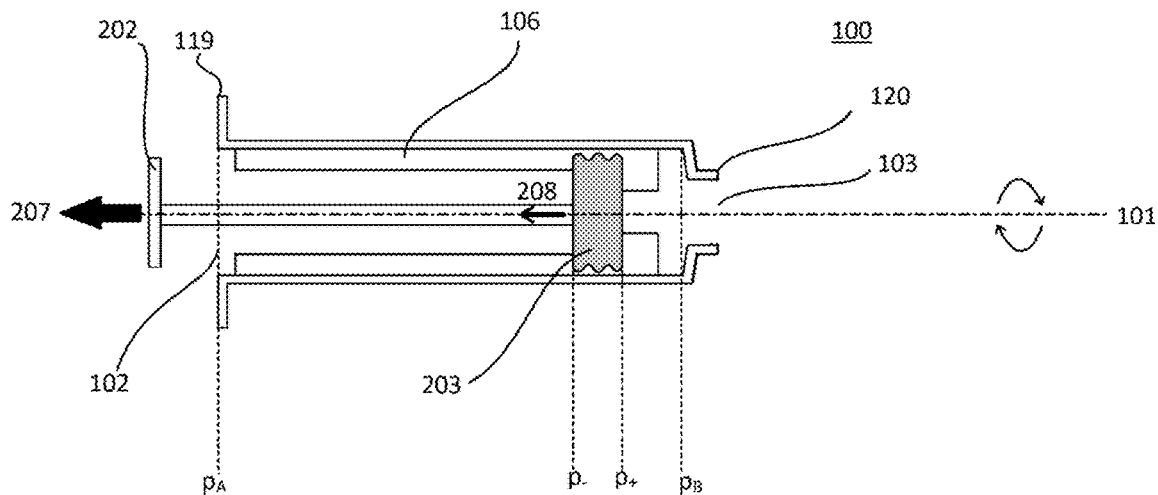

FIG. 4C shows the receptacle 100 immediately after the pushing force 207 exceeds the stiction force at axial position $p_+$ to put the charge 203 into motion. The charge 203 is still at axial position $p_+$, but is in motion 208 along the axis 101. The pushing force 207 is equal to the dynamic friction at axial position $p_+$ and the charge 203 is in a state of constant velocity along the axis 101.

Figure 4D:
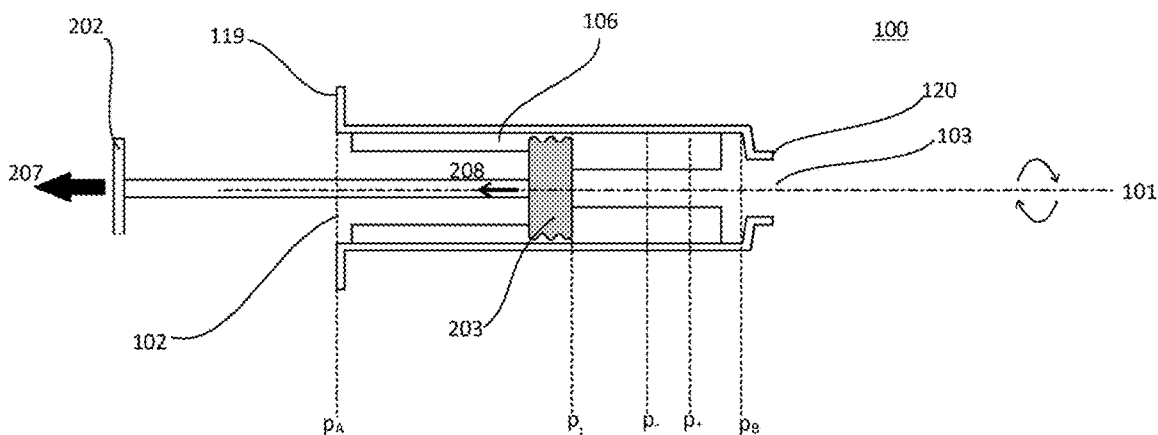

FIG. 4D shows the receptacle 100 subsequent to that of FIG. 4C, in which the charge 203 has travelled a distance from $p_+$ to $p_1$ along the axis 101. The charge 203 is still in motion 208 with constant velocity with the pulling force 207 being equal to the dynamic friction at axial position $p_1$. Therefore, the pulling force is a measure of the dynamic friction at axial position $p_1$.

Figure 4E:
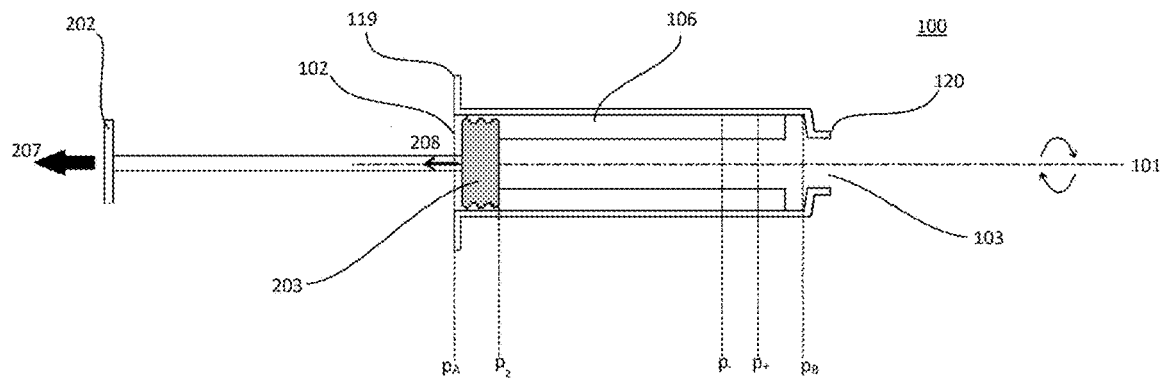

FIG. 4E shows the receptacle 100 after the situation of FIG. 4D. The charge 203 has travelled a further distance from $p_1$ to $p_2$ along the axis 101. $p_2$ is close to the first aperture 102 at the first end 119. The charge is still in motion with constant velocity with the pushing force 207 and the dynamic friction being equal. The pushing force 207 is thus a measure of the dynamic friction at axial position $p_2$.

Figure 4F:
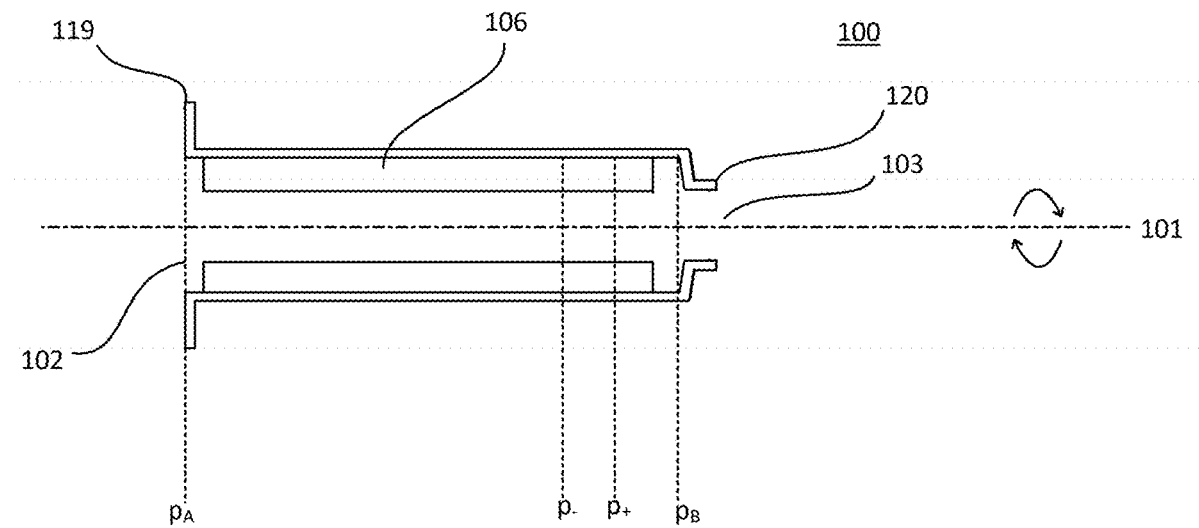

FIG. 4F shows the receptacle 100 after the charge 203 has left through the first aperture 102.

The dynamic friction at any point along the axis 101 is provided directly as the pushing force 207 required at that point to maintain constant velocity (100 mm/min) of the charge 203 along the axis 101. The dynamic friction at points $p_+$, $p_1$ and $p_2$ are measured at the stages of FIGS. 4C, 4D and 4E respectively.

Figure 5:
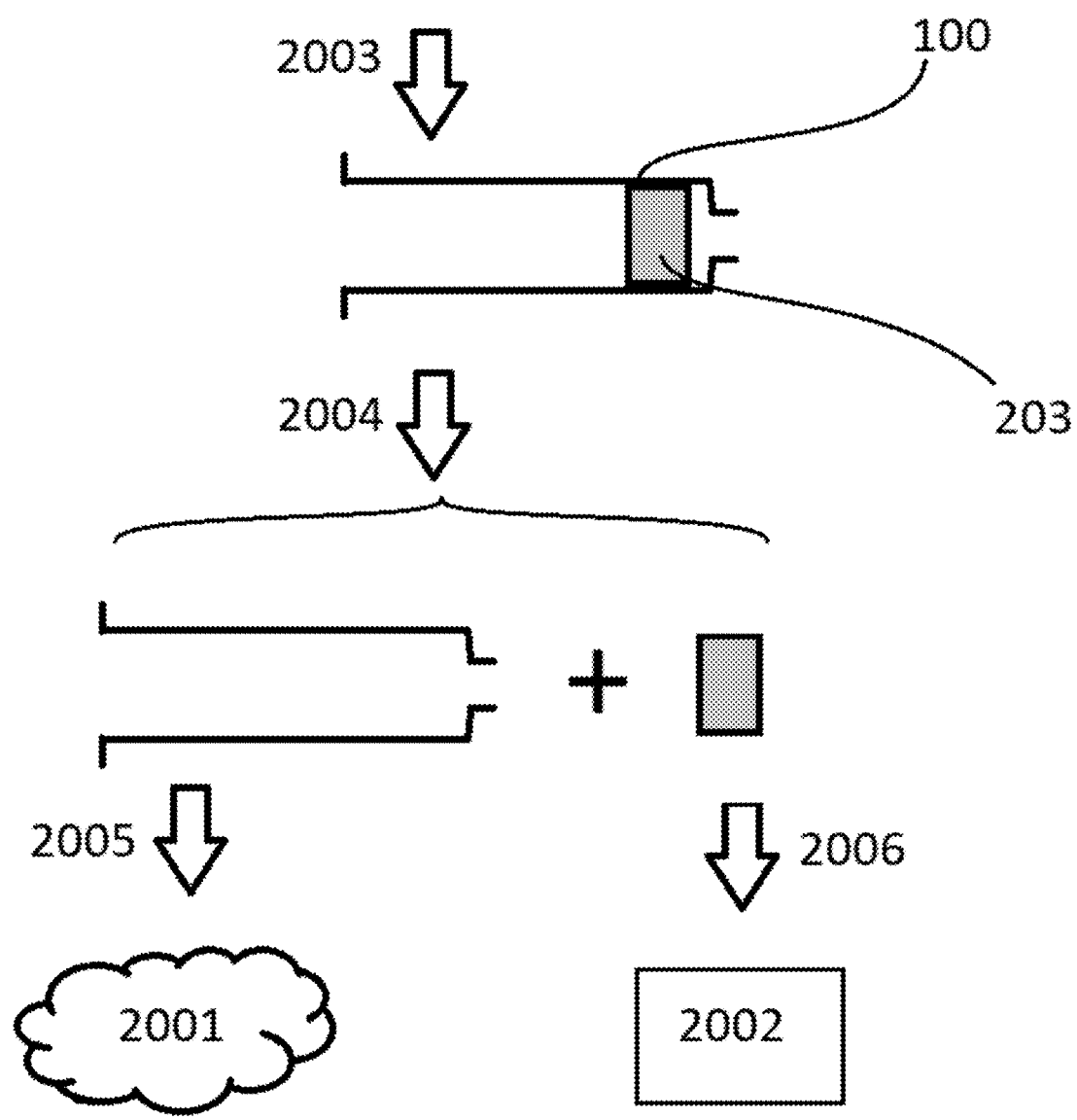
FIG. 5 illustrates a schematic for a disposal process.

FIG. 5 shows a schematic for a disposal process. In a first step 2003, a receptacle provided according to the present invention is provided. In a second step 2004, the charge 203 is removed from the receptacle. The receptacle 100 without charge 203 is then incinerated in a step 2005 to obtain a disposal product 2001, which is a gaseous combustion product. The charge 203, which contains butyl rubber, can be disposed of separately in a step 2006 to obtain a further disposal product 2002. In some embodiments, the step 2006 is not a combustion step. The process allows a gaseous combustion product 2001 which is free of or has a reduced content of halogen.

Figure 6:
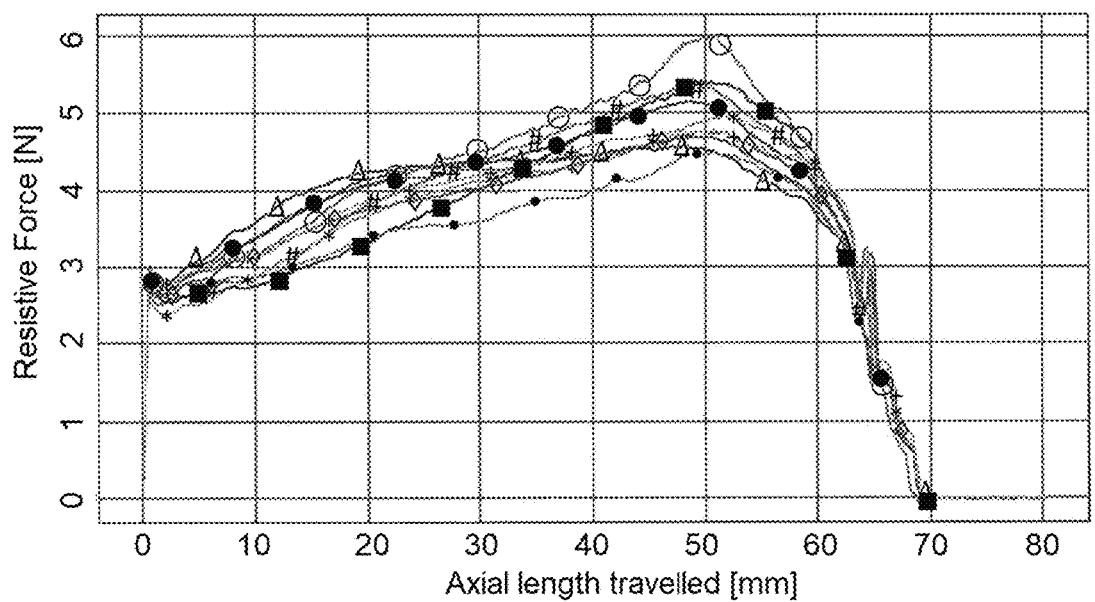
FIG. 6 illustrates a dynamic force profile for an exemplary embodiment of a syringe provided according to the present invention, which is designated as Example 1.

FIG. 6 shows a dynamic force profile for 10 runs of Example 1 from the examples section. Axial position of the charge 203 is presented in the direction from $p_B$ to $p_A$ with $p_+$ as zero point. A maximum of around 4.5 to 6 N is shown at around 50 mm from the start point. A minimum of around 2.5 to 3 N is shown at the start of the run.

Figure 7A:
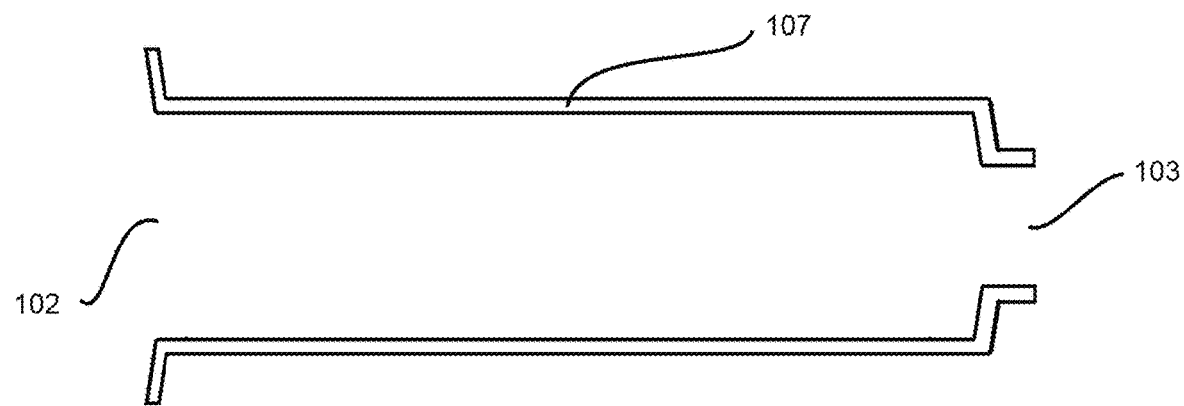
FIGS. 7A to 7F illustrate an exemplary embodiment of a process for preparing receptacles provided according to the present invention.
Figure 7B:
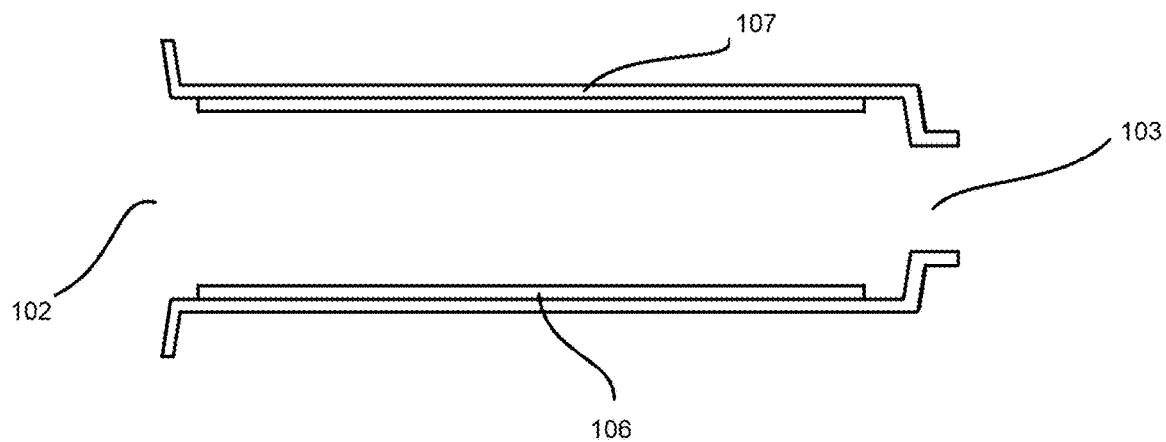
Figure 7C:
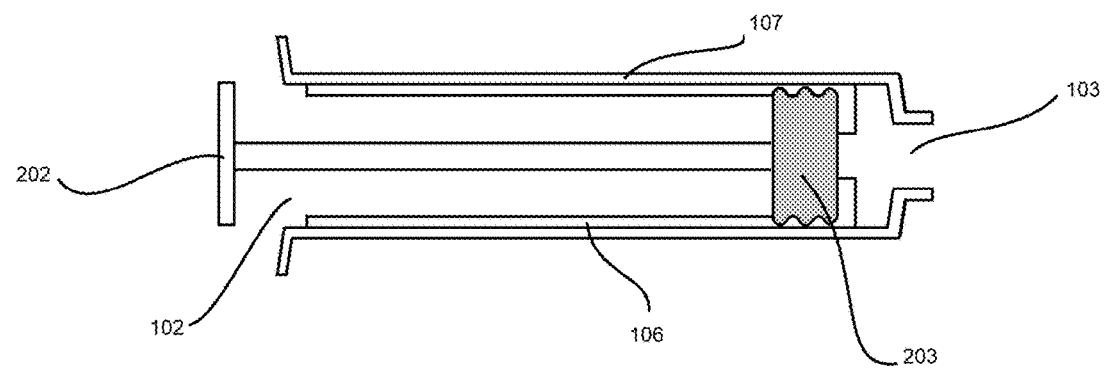
Figure 7D:
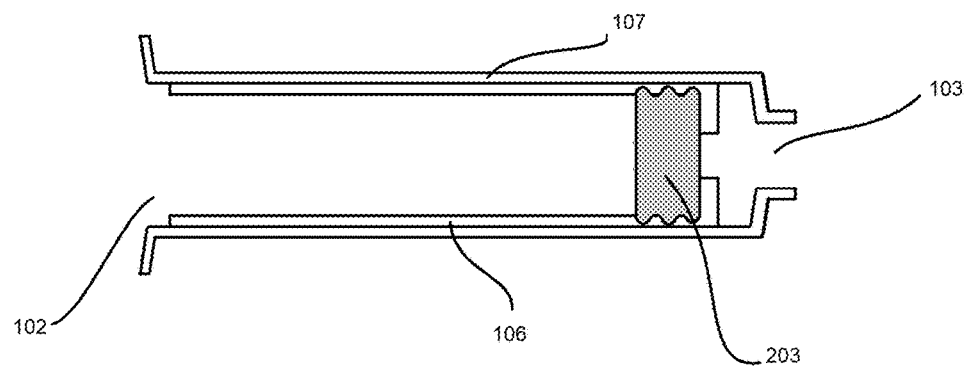
Figure 7E:
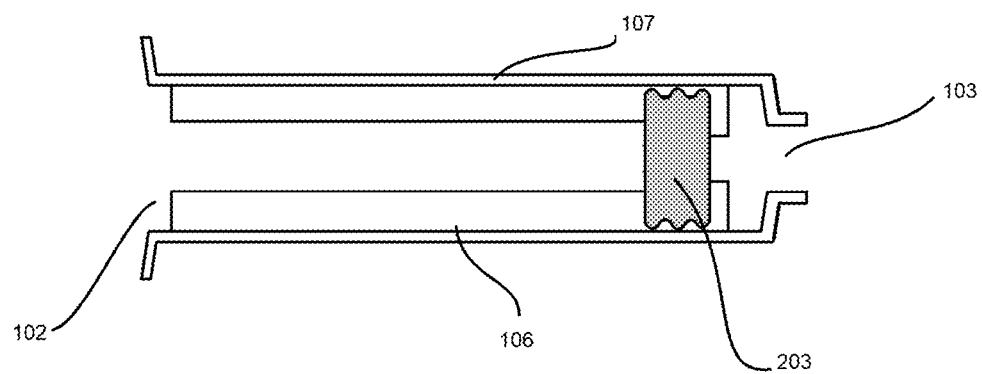
Figure 7F:
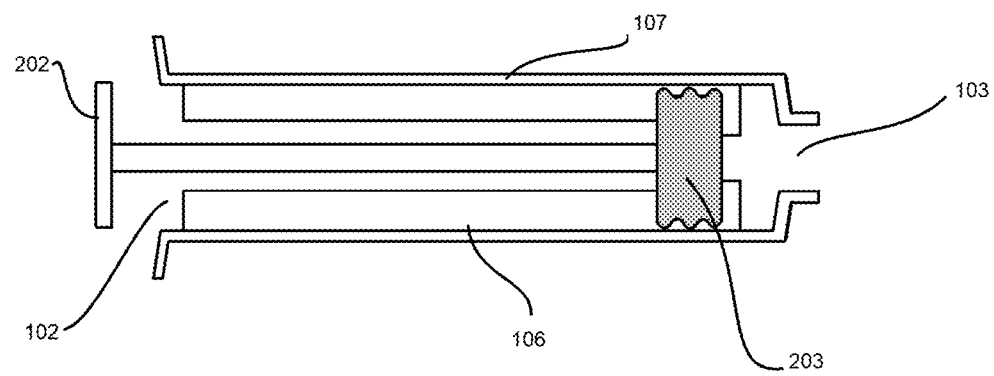

FIGS. 7A to 7F show the process for preparing the receptacles for the examples. FIG. 7A shows an empty receptacle having a plastic side wall 107, a first aperture 102 and a second aperture 103. A relatively thin lubricant layer 106 is applied to the inner surface of the side wall 107 as shown in FIG. 7B, in this case a layer of mean thickness 20 nm. The 20 nm layer of lubricant is applied by spraying. A charge 203 is provided. The charge 203 has a flexible bromo-butyl rubber surface and has an elongate rod 202 attached by screwing. The charge 203 and the elongate rod 202 together act as a plunger. The elongate rod 202 is used to push the charge 203 into the receptacle via the first aperture 102 and within the receptacle to arrive close to the second aperture 103, as shown in FIG. 7C. The lubricant layer 106 facilitates movement of the charge 203 inside the receptacle by reducing friction with the side wall 107. Some lubricant may be pushed forward by the charge 203 and accumulates in front of the charge 203. An exaggerated increase in the thickness of the lubricant layer 106 in front of the charge 203 is shown in FIG. 7C for illustration purposes. Accordingly, the thickness of the lubricant layer 106 behind the charge is reduced below the original value of 20 nm. The elongate rod 202 is unscrewed from the charge 203 to facilitate access to the interior of the receptacle, as shown in FIG. 7D, where the charge 203 is still inside the receptacle, close to the second aperture 103, but the elongate rod 202 has been removed. The thickness of the lubricant layer 106 is then adapted by adding or removing lubricant material. Lubricant material is added by spraying. Lubricant material is removed using a wiping tool, such as a tampon. The thickness profile of the lubricant layer 106 is adapted to the profiles presented in the examples. FIG. 7E shows the case where the thickness of the lubricant layer 106 has been increased through addition of further lubricant. Once the required thickness profile has been achieved, the lubricant layer is cured by heating at 175° C. for 20 seconds. FIG. 7F shows the receptacle with the elongate rod 202 screwed back onto the charge 203 to allow it to function as a plunger.

Test Methods

Layer Thickness

The thickness of the layer is determined by optical interference measurements using the RapID Explorer available from rap.ID Particle Systems GmbH. Measurements are taken from outside the receptacle through the side wall. The device is operated with the proprietary software and in accordance with the 2014 proprietary instruction manual.

Resistive Force

Resistive force is measured using a TesT 106.2 kN device commercially available from TesT GmbH, Germany. The charge was moved with a speed of 100 mm/minute.

EXAMPLES

The following examples are for further elucidation of embodiments provided according to the present invention and do not limit the scope of the claimed invention.

A lubricant was prepared as follows: 10 g of a vinyl-functionalized polydimethylsiloxane were initially charged in a reaction vessel and admixed with 65 g of decamethyl-cyclopentasiloxane. Under constant stirring at 800 rpm, 0.5 g of methylhydrosiloxane/dimethylsiloxane copolymer, 6.25 g of liquid polydimethylsiloxane, 0.01 g of 10% hexachloroplatinic acid in isopropanol as catalyst and 0.05 g of 2,4,7,9-tetramethyl-5-decyne-4,7-diol as inhibitor were added to this reaction mixture. The reaction solution was used after a stirring time of 60 s. A receptacle was provided according to FIG. 2 using the method presented in FIGS. 7A to 7F. The receptacle was a 1 ml 1g TopPac available from Schott AG Germany. The thickness profile of the applied layer was according to Table 1. The charge was a bromo butyl rubber stopper FM 257/2 available from Dedecke GmbH, Germany. A process similar to that displayed in FIGS. 4A to 4F was performed to determine the dynamic friction along the barrel. The TesT 106.2 kN device commercially available from TesT GmbH, Germany was employed. Values at 10, 20, 50 and 60 mm along the barrel are displayed in Table 2. The constant velocity of the charge during the measurement movement was 100 mm/min. Axial positions in the barrel are presented in a direction from $p_B$ to $p_A$, with $p_+$ as the zero point. For each of the Examples 1 to 5, a batch of 50 syringes was tested.

TABLE 1

| | Distance along barrel [mm] | | | | | | |
|---|---|---|---|---|---|---|---|
| Example | 0 | 10 | 20 | 30 | 40 | 50 | 60 |
| | Thickness t [nm] | | | | | | |
| 1 | 202 | 240 | 222 | 120 | 90 | 50 | 43 |
| 2 | 8 | 10 | 9 | 7 | 4 | 3 | 3 |
| 3 | 988 | 1269 | 860 | 732 | 480 | 337 | 298 |
| 4 | 2014 | 2005 | 1998 | 2104 | 1962 | 2008 | 1989 |

TABLE 2

| | Distance along barrel [mm] | | | |
|---|---|---|---|---|
| Example | 10 | 20 | 50 | 60 |
| | Dynamic friction [N] | | | |
| 1 | 3.1 | 3.4 | 6.2 | 4.8 |
| 2 | 9.2 | 9.1 | 9.1 | 9.7 |
| 3 | 2.8 | 2.7 | 3.3 | 3.1 |
| 4 | 3.1 | 2.8 | 3.0 | 2.9 |

The receptacles were used to draw in a small amount of liquid and release it. The charges were then removed from the receptacles ready for the receptacles to be incinerated. The force profile in Example 1 provided a useful haptic feedback which allowed for fine control of the syringe, even without having to look at the syringe whilst drawing fluid. This is particularly useful for merging a medical liquid with bodily fluid when introducing medical liquid into the body of a patient. The charge could be easily removed from the syringe of Example 1 before incineration. The empty receptacle could then be incinerated with no halogen content in the disposal gas.

The syringe of Example 2 offered too much resistance for controlled drawing of liquid into the syringe. The charge was difficult to remove from the receptacle and on occasions jammed. Receptacles with charges still inside had to be crushed and manually sorted to remove the charge before incineration so as to avoid halogen content in the disposal gas.

The syringes of Examples 3 & 4 did allow drawing of liquid into the syringe. In both cases, controlled drawing of liquid was more difficult than for Example 1 due to the lack of haptic feedback. Controlled drawing was not possible whilst looking away from the syringe. The charge could be easily removed in both Examples 3 and 4. During storage of the syringes of Examples 2 and 3, however, some of the charges fell from the receptacle, spilling remaining pharmaceutical liquid.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A receptacle for pharmaceutical packaging, the receptacle comprising:
   an elongate barrel section having a direction of elongate extension and an axis in the direction of elongate extension, an axial position p being determined along the axis, the elongate barrel section extending from an axial position $p_A$ to an axial position $p_B$, the elongate barrel section defining a barrel length $L_B$ which is the distance between the axial position $p_A$ and the axial position $p_B$;
   a first end closer to the axial position $p_A$ than to the axial position $p_B$;
   a second end closer to the axial position $p_B$ than to the axial position $p_A$;
   a first aperture at the first end that has a first aperture diameter;
   a second aperture at the second end that has a second aperture diameter, the first aperture diameter is greater than the second aperture diameter;
   a plurality of side walls extending over the elongate barrel section, the side walls each having an inner surface bordering an interior, the interior having a diameter;
   a layer of a lubricant located on at least a part of the inner surface, wherein, at a given axial position p on the axis between the axial position $p_A$ and the axial position $p_B$, a thickness of each side wall, a thickness of the layer, and the diameter of the interior are each determined as an angular mean in a cross-sectional plane perpendicular to the axis at the axial position p; and
   a charge present in the interior and sealing a cross section of the interior between the inner surfaces of the side walls, an axial position $p_+$ being the axial position closest to the axial position $p_B$ at which the charge contacts the layer or the inner surfaces and an axial position $p_-$ being the axial position closest to the axial position $p_A$ at which the charge contacts the layer or the inner surfaces, a value of the distance between the axial position $p_B$ and the axial position $p_+$ divided by the distance between the axial position $p_+$ and the axial position $p_A$ is in a range from 0 to 2, a mean thickness of the layer determined between the axial position $p_A$ and the axial position p. is at least 10 nm, wherein at least one criteria is satisfied, the at least one criteria being selected from the group consisting of:
 the length $L_B$ is in a range from 3 cm to 20 cm;
 a mean value of the diameter of the interior determined over a range from the axial position $p_A$ to the axial position $p_B$ is in a range from 0.4 cm to 4 cm;
 a mean thickness of one of the sidewalls determined over a range from the axial position $p_A$ to the axial position $p_B$ is in a range from 0.3 mm to 4.5 mm; and
 the volume of the interior is in a range from 0.1 to 150 ml.

2. The receptacle of claim 1, wherein the mean thickness of the layer determined between the axial position $p_A$ and the axial position $p_-$ is at most 300 nm.

3. The receptacle of claim 2, wherein the mean thickness of the layer determined between the axial position $p_A$ and the axial position $p_-$ is at most 100 nm.

4. The receptacle of claim 1, wherein a maximum thickness of the layer determined between the axial position $p_A$ and the axial position $p_-$ is at an axial position closer to the axial position $p_-$ than to the axial position $p_A$.

5. The receptacle of claim 1, wherein the mean thickness of the layer determined between the axial position $p_B$ and the axial position $p_+$ is at least 1.5 times the mean thickness of the layer determined between the axial position $p_A$ and the axial position $p_-$.

6. The receptacle of claim 1, wherein the charge comprises a halogen.

7. The receptacle of claim 6, wherein the halogen is present in a coating of the charge.

8. The receptacle of claim 1, wherein a maximum force required to remove the charge from the receptacle through the first aperture is not more than 10 N.

9. The receptacle of claim 8, wherein the maximum force required to remove the charge from the receptacle through the first aperture occurs when a front of the charge is closer to the axial position $p_A$ than to the axial position $p_B$.

10. The receptacle of claim 8, wherein the maximum force required to remove the charge from the receptacle through the first aperture is at least 4 N.

11. The receptacle of claim 10, wherein the maximum force required to remove the charge from the receptacle through the first aperture is not more than 7 N.

12. The receptacle of claim 1, wherein the lubricant comprises one or more silicone oils.

13. The receptacle of claim 12, wherein the one or more silicone oils are at least partially contained in a matrix bound to the inner surface.

14. The receptacle of claim 1, further comprising a liquid pharmaceutical composition present in a section of the interior between the axial position $p_+$ and the axial position $p_B$.

15. The receptacle of claim 1, wherein a maximum thickness of the layer determined between the axial position $p_B$ and the axial position $p_+$ is at least 1.5 times a maximum thickness of the layer determined between the axial position $p_A$ and the axial position p.

16. The receptacle of claim 1, wherein a continuous portion between the axial position $p_A$ and the axial position $p_-$ having a length of at least 50% of the length from the axial position $p_A$ and the axial position $p_-$ has a minimum thickness and a maximum thickness and a difference between the minimum thickness and the maximum thickness is at least 5 nm.

17. The receptacle of claim 16, wherein the difference between the minimum thickness and the maximum thickness is at most 300 nm.

18. The receptacle of claim 1, wherein the layer extends over at least 70% of the barrel length $L_B$.

19. A process for preparing a disposal product, the process comprising:
 providing a receptacle, the receptacle comprising:
  an elongate barrel section having a direction of elongate extension and an axis in the direction of elongate extension, an axial position p being determined along the axis, the elongate barrel section extending from an axial position $p_A$ to an axial position $p_B$, the elongate barrel section defining a barrel length $L_B$ which is the distance between $p_A$ and $p_B$;
  a first end closer to the axial position $p_A$ than to the axial position $p_B$;
  a second end closer to the axial position $p_B$ than to the axial position $p_A$;
 a first aperture at the first end that has a first aperture diameter;
  a second aperture at the second end that has a second aperture diameter, the first aperture diameter is greater than the second aperture diameter;
  a plurality of side walls extending over the elongate barrel section, the side walls each having an inner surface bordering an interior, the interior having a diameter;
  a layer of a lubricant located on at least a part of the inner surface, wherein, at a given axial position p on the axis between the axial position $p_A$ and the axial position $p_B$, a thickness of each side wall, a thickness of the layer, and the diameter of the interior are each determined as an angular mean in a cross-sectional plane perpendicular to the axis at the axial position p; and
  a charge present in the interior and sealing a cross section of the interior between the inner surfaces of the side walls, an axial position $p_+$ being the axial position closest to the axial position $p_B$ at which the charge contacts the layer or the inner surfaces and an axial position $p_-$ being the axial position closest to the axial position $p_A$ at which the charge contacts the layer or the inner surfaces, a value of the distance between the axial position $p_B$ and the axial position $p_+$ divided by the distance between the axial position $p_+$ and the axial position $p_A$ is in a range from 0 to 2, a mean thickness of the layer determined between the axial position $p_A$ and the axial position p. is at least 10 nm, wherein at least one criteria is satisfied, the at least one criteria being selected from the group consisting of:
   the length $L_B$ is in a range from 3 cm to 20 cm;
   a mean value of the diameter of the interior determined over a range from the axial position $p_A$ to the axial position $p_B$ is in a range from 0.4 cm to 4 cm;
   a mean thickness of one of the sidewalls determined over a range from the axial position $p_A$ to the axial position $p_B$ is in a range from 0.3 mm to 4.5 mm; and
   the volume of the interior is in a range from 0.1 to 150 ml; and
 converting the receptacle into the disposal product.

20. A receptacle for pharmaceutical packaging, comprising:
- an elongate barrel section having a direction of elongate extension and an axis in the direction of elongate extension, an axial position p being determined along the axis, the elongate barrel section extending from an axial position $p_A$ to an axial position $p_B$;
- a first end closer to the axial position $p_A$ than to the axial position $p_B$;
- a second end closer to the axial position $p_B$ than to the axial position $p_A$;
- a first aperture at the first end that has a first aperture diameter;
- a second aperture at the second end that has a second aperture diameter, the first aperture diameter is greater than the second aperture diameter;
- a plurality of side walls extending over the elongate barrel section, the side walls each having an inner surface bordering an interior that defines a volume;
- a layer of lubricant placed on at least a part of the inner surface; and
- a charge present in the interior and sealing a cross section of the interior between the inner surfaces of the side walls, the charge being displaceable within the interior between the axial position $p_B$ and the axial position $p_A$ and removeable from the interior by pulling the charge out of the interior through the first aperture, a variable dynamic friction being defined between the charge and the side walls as the charge is displaced between the axial position $p_B$ and the axial position $p_A$, the dynamic friction increasing as the charge is displaced in a first region of the interior in a direction from the axial position $p_B$ toward the axial position $p_A$ and decreasing as the charge is displaced in a second region of the interior in the direction from the axial position $p_B$ toward the axial position $p_A$.

* * * * *